(12) United States Patent
Whack

(10) Patent No.: US 10,799,399 B1
(45) Date of Patent: Oct. 13, 2020

(54) TIME-RELEASED TAMPON APPLICATOR

(71) Applicant: Sonya D. Whack, Florence, SC (US)

(72) Inventor: Sonya D. Whack, Florence, SC (US)

( * ) Notice: Subject to any disclaimer, the term of this patent is extended or adjusted under 35 U.S.C. 154(b) by 314 days.

(21) Appl. No.: 15/974,940

(22) Filed: May 9, 2018

(51) Int. Cl.
*A61F 13/20* (2006.01)
*A61F 13/26* (2006.01)
*A61L 15/44* (2006.01)
*A61K 9/00* (2006.01)

(52) U.S. Cl.
CPC ...... *A61F 13/2085* (2013.01); *A61F 13/2074* (2013.01); *A61F 13/26* (2013.01); *A61K 9/0036* (2013.01); *A61L 15/44* (2013.01); *A61F 13/2022* (2013.01); *A61L 2300/602* (2013.01)

(58) Field of Classification Search
CPC .. A61F 13/2022; A61F 13/2074; A61F 13/26; A61F 13/28; A61F 2013/15097; A61F 6/08; A61F 6/12; A61K 9/0034; A61K 9/0036
See application file for complete search history.

(56) References Cited

U.S. PATENT DOCUMENTS

| 4,286,596 | A | * | 9/1981 | Rubinstein ............ A61F 5/0093 604/12 |
| 4,318,405 | A | | 3/1982 | Sneider |
| 5,542,914 | A | * | 8/1996 | Van Iten ............. A61F 13/2051 604/11 |
| 6,558,362 | B1 | * | 5/2003 | Chaffringeon ........ A61M 31/00 604/287 |
| 7,815,594 | B2 | * | 10/2010 | Dougherty, Jr. ........ A61F 13/26 604/17 |
| 7,993,667 | B2 | | 8/2011 | Gehling et al. |
| 9,615,977 | B2 | * | 4/2017 | Levantino ........... A61F 13/2074 |

* cited by examiner

*Primary Examiner* — Catharine L Anderson
(74) *Attorney, Agent, or Firm* — Sanchelima & Associates, P.A.; Christian Sanchelima; Jesus Sanchelima

(57) ABSTRACT

The present invention is a time-released tampon applicator that is capable of releasing a medicated cream/ointment inside vagina to relieve yeast infection. The time-released tampon applicator of the present invention can release the medication throughout the day and avoids the messiness associated with conventional administration of medication towards vaginal yeast infection.

6 Claims, 1 Drawing Sheet

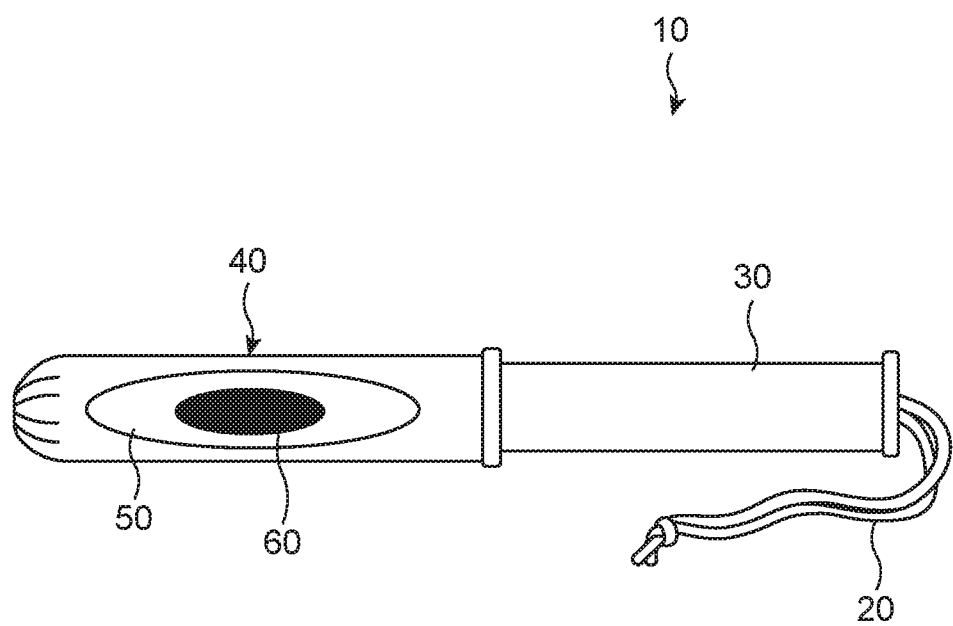

TIME-RELEASED TAMPON APPLICATOR

BACKGROUND OF THE INVENTION

1. Field of the Invention

The present disclosure relates to a device for releasing medication in vagina. More particularly, the present disclosure relates to a tampon applicator that releases a measured quantity of medication in a timely manner in vagina.

2. Description of the Related Art

In a female vagina, when yeast cells outnumber bacteria cells, female vagina is likely to be infected by yeast infection which can be treated by introducing antifungal medicine (in form of creams, tablets, ointments or suppositories) multiple times in a day in the female vagina. However, the administration of the antifungal medicine becomes especially messy and inconvenient, if the antifungal medicine is in the form of ointment/cream. Also, it is likely that one may forget insertion of antifungal medicine.

Several designs for medicated tampons to treat vaginal infections have been designed in the past. None of them, however, include a medicated tampon applicator that would release the required dosage of the medicine in a timely manner.

Applicant believes that a related reference corresponds to U.S. Pat. No. 4,318,405 filed by Vincent R. Sneider for a tampon and drug delivery device. However, the tampon disclosed by Vincent R. Sneider is specifically for a delivery of a capsule and further does not contain the provision for time release of medication.

Another related reference is U.S. Pat. No. 7,993,667 filed by Kimberly-Clark Worldwide Inc. The reference by Kimberly-Clark Worldwide Inc. describes methods of manufacturing a medicated tampon assembly. However, the method taught by Kimberly-Clark Worldwide Inc. is complex and does not provide a timely release of the medication.

Other references describing the closest subject matter provide for a number of more or less complicated features that fail to solve the problem in an efficient and economical way. There are no known references that suggest the novel features of the present invention.

SUMMARY OF THE INVENTION

It is yet another object of the present invention is to provide a tampon applicator that releases a measured quantity of a medication in a time-released manner.

It is still another object of the present invention to provide a time-released tampon applicator containing a medication to alleviate the symptoms of vaginal itching by reducing user's efforts and time without experience messy feeling and inconvenience.

Further objects of the invention will be brought out in the following part of the specification, wherein detailed description is for the purpose of fully disclosing the invention without placing any limitations thereon.

BRIEF DESCRIPTION OF THE DRAWING

With the above and other related objects in view, the invention consists in the details of construction and combination of parts as will be more fully understood from the following description, when read in conjunction with the accompanying drawing in which:

FIG. 1 represents a schematic illustration of a time-released tampon applicator of the present invention containing a medication for treating yeast infection.

DETAILED DESCRIPTION OF THE EMBODIMENTS OF THE INVENTION

The present disclosure envisages a time-released tampon applicator. The time-released tampon applicator is capable of releasing a medicated cream/ointment inside the vagina of a female to alleviate the symptoms of yeast infection.

The time-released tampon applicator would release the medication (cream/ointment) inside the vagina to alleviate the symptoms of yeast infection.

Referring now to the drawing, FIG. 1, where the present invention is generally referred to with numeral 10, it can be observed that a time-released tampon applicator, in accordance with one embodiment, is provided that includes a string 20, plunger 30, holder 40, and tampon 50.

String 20 helps in the proper placing and removal of the tampon from vagina. Preferably, string 20 is mounted to plunger 30.

Plunger 30 aids in the proper positioning and release of the tampon in the body.

Holder 40 holds the tampon that is to be inserted in the body.

The center of the tampon 50 comprises a medicated suppository 60 that would release cream/ointment into the vagina to treat a yeast infection. Medicated suppository 60 will be covered by a thin-layered tampon.

The time-released tampon is introduced in the vaginal to dispense the time-released medication through the course of the day, and thereby avoids the mess/leakage present by conventional application of the medication to the vagina.

The medication against the yeast infection is released in a timely manner as per the required dosage and brings relief to the symptoms of yeast infection. The time-released tampon applicator of the preset invention is capable of releasing the medication throughout the day, as it has a "time-release" mechanism.

Typically, the time-released tampon applicator 10 of the present invention has a height in the range of 3 inches to 6 inches. Various types of medications having different strength/concentration may be used to treat yeast infection of vagina using the time-released tampon applicator of the present invention.

Time-released tampon applicator 10 of the present invention is simple and cost effective and can be easily used by women of all ages for the treatment of vaginal yeast infection. Time-released tampon applicator 10 thus releases medication at regular time interval to alleviate the symptoms of vaginal itching by reducing user's efforts and time without experience messy feeling and inconvenience caused to user.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:
1. A tampon applicator, comprising:
a tubular housing adapted to be inserted into a user's vagina; said housing includes a holder telescopically mounted to a plunger, said holder includes a sidewall having a sidewall opening; a tampon housed within said holder, said tampon having a center that includes a medicated suppository having a medication; said holder including a distal end having a distal end opening adapted to allow said tampon to absorb fluids through said distal end opening; said sidewall opening partially reveals said tampon, said medicated suppository being entirely revealed through said sidewall opening, said medication configured to be time released into said user's vagina.

2. The tampon applicator of claim 1 wherein said plunger includes a string mounted thereon, said string having a length adapted to allow a user to easily remove said tampon applicator from said user's vagina.

3. The tampon applicator of claim 1 wherein said tampon has a thin tampon layer covering said medicated suppository.

4. The tampon applicator of claim 3 wherein said thin tampon layer is porous and is adapted to allow said medication to seep through.

5. The tampon applicator of claim 1 wherein said plunger includes a plunger length adapted to permit a user to easily insert said tampon applicator into said vagina.

6. The tampon applicator of claim 1 wherein said medication is adapted to be delivered entirely inside said vagina.

\* \* \* \* \*